(12) United States Patent
Deng et al.

(10) Patent No.: US 10,694,979 B2
(45) Date of Patent: Jun. 30, 2020

(54) PATIENT WITH ALZHEIMER'S DISEASE POSITIONING AND RETRIEVAL ASSEMBLY CARRYING AN ORIGINAL LOCATION

(71) Applicant: DONGGUAN UNIVERSITY OF TECHNOLOGY, Dongguan (CN)

(72) Inventors: Jun Deng, Dongguan (CN); Mengyao Lai, Dongguan (CN)

(73) Assignee: DONGGUAN UNIVERSITY OF TECHNOLOGY, Dongguan (CN)

( * ) Notice: Subject to any disclaimer, the term of this patent is extended or adjusted under 35 U.S.C. 154(b) by 0 days.

(21) Appl. No.: 16/440,819

(22) Filed: Jun. 13, 2019

(65) Prior Publication Data
US 2019/0388010 A1  Dec. 26, 2019

(30) Foreign Application Priority Data
Jun. 22, 2018  (CN) .......................... 2018 1 0649003

(51) Int. Cl.
*H05K 7/02* (2006.01)
*H05K 7/04* (2006.01)
(Continued)

(52) U.S. Cl.
CPC .......... *A61B 5/1112* (2013.01); *A61B 5/6831* (2013.01); *A61B 5/746* (2013.01);
(Continued)

(58) Field of Classification Search
USPC ............... 361/809; 455/456, 457; 340/572.1, 340/573.4, 539.1, 539.11
See application file for complete search history.

(56) References Cited

U.S. PATENT DOCUMENTS

| | | | |
|---|---|---|---|
| 8,115,621 B2* | 2/2012 | Rajala ..................... | G01S 1/042 340/539.11 |
| 2011/0109461 A1* | 5/2011 | Aninye ............... | G08B 21/0288 340/573.4 |
| 2020/0085321 A1* | 3/2020 | Hatch ................. | A61M 16/024 |

* cited by examiner

Primary Examiner — Hung S. Bui
(74) Attorney, Agent, or Firm — Law Offices of Steven W Weinrieb (57) ABSTRACT

The present invention relates to a patient with Alzheimer's disease positioning and retrieval assembly carrying an original location, including a sealing box, the upper part of the sealing box is the control part, and the lower part thereof is the display part. The locking outer plate, is fixedly connected to an alarm device communicating with the control part; the display part includes a display positioning sleeve provided within the sealing box. The display positioning sleeve comprises a display glass sleeve, a display sealing block and a display pressing column from front to back. The display glass sleeve is internally sleeved sealingly with a horizontal display glass block, a cardboard is disposed between the display sealing block and the display glass block, the front panel of the sealing box is provided with a display port fitting the display glass block. In the present invention, the control part of the power distribution control box is connected with the alarm device, and the display part of the power distribution control box displays the initial position, thereby it is convenient for people to find the patients and send them back. In addition, sealing of the display part is done by mechanical sealing structure and glass pate, and the original position is displayed by a written paper, thereby energy consumption is low.

10 Claims, 5 Drawing Sheets

(51) Int. Cl.
*A61B 5/11* (2006.01)
*A61B 5/00* (2006.01)
*H05K 5/00* (2006.01)
*H05K 5/02* (2006.01)
*G08B 21/02* (2006.01)

(52) U.S. Cl.
CPC ......... *A61B 5/7445* (2013.01); *H05K 5/0017* (2013.01); *H05K 5/0086* (2013.01); *H05K 5/0221* (2013.01); *A61B 2503/08* (2013.01); *G08B 21/0288* (2013.01)

PATIENT WITH ALZHEIMER'S DISEASE POSITIONING AND RETRIEVAL ASSEMBLY CARRYING AN ORIGINAL LOCATION

FIELD OF THE INVENTION

The present invention relates to the field of positioning equipment, more particularly relates to a patient with Alzheimer's disease positioning and retrieval assembly carrying an original location.

BACKGROUND OF THE INVENTION

China is the world's largest populous country, with a large population at all levels, and the number of the elderly people over 60 is over 100 million. In this group of people, some people suffer from Alzheimer's disease or intermittent Alzheimer's disease. Alzheimer's patients need to be cared for at all times. They will be lost if they have not been taken good care of. Often notices for looking for a person can be seen in the streets, but the result is seldom satisfactory.

Today, when electronic equipment is so developed, there should be no loss of old people. Various locators and trackers, and the like, have appeared in the market, but they have obvious defects and need to be positioned by satellite, so it is only suitable for places with good signals. Moreover, they require power input and cannot achieve long-term positioning, and as the lost old people cannot charge it, and it's liable to be lost under grabbing of the wearer, the trackers or locators cannot function as we wish, and the old people missing is still a serious social problem.

OVERALL OBJECTIVE OF THE INVENTION

The overall objective of the invention is to provide a patient with Alzheimer's disease positioning and retrieval assembly carrying an original location, wherein the control part of the power distribution control box is connected with the alarm device, and the display part of the power distribution control box displays the initial position, thereby it is convenient for people to find the elderly and send them back. And the display part adopts a mechanical sealing structure and a glass plate to achieve sealing, and the original position is displayed by a written paper, thereby saving energy consumption.

In order to achieve the above objective, the technical solution adopted by the present invention is as follows:

A patient with Alzheimer's disease positioning and retrieval assembly carrying an original location, including a power distribution control box with hanging straps attached to both sides thereof, the two hanging straps are respectively connected with a locking outer plate and a locking inner plate; the power distribution control box includes a openable sealing box locked by box locking bolts, the inner upper part of the sealing box is a control part, the lower part of the sealing box is a display part; the locking outer plate is connected to an alarm device communicating with the control part; the display part includes a display positioning sleeve provided within the sealing box; the display positioning sleeve is internally provided with a display glass sleeve, a display sealing block and a display pressing column from front to back; the front part of the display sealing blocks is provided with sealing block positioning convex rings plug-in fitted with the display glass sleeves; the display glass sleeve is internally sleeved sealingly with a horizontal display glass block, a cardboard is disposed between the display sealing block and the display glass block, the front panel of the sealing box is provided with a display port fitting the display glass block.

Further, a display barrier net is fixedly connected to the display port by barrier locking bolts, the mesh of the display barrier net is smaller than dimension of fingertips.

Further, the display press block is internally provided with horizontally oriented pressing holes; the rear part of the display sealing block is provided with sealing block locating pillars plug-in fitted with the pressing holes, the rear side of the sealing block locating pillars is provided with display pressing springs in compression state, the rear side of the display pressing springs is connected to display pressing pillars, which are sealingly fitted with the pressing holes and the rear ends thereof are inserted into the rear plate of the sealing box.

Further, the outer ends of the locking inner plate are provided with interference fitting pillars interference fitting with the locking outer plate; one connection column of the alarm device is connected to the control part by the locking outer plate and a conductor wire provided within the hanging strap, and another connection column thereof is interference fitted with the interference fitting pillar, and the interference fitting pillar is connected to the control part by the locking inner plate and the conductor wire provided within the hanging strap, the control part is a power distribution control element that controls the alarm device to operate intermittently.

Further, the control part includes a storage battery disposed within the sealing box, the upper part of the storage battery is connected to a controller with battery connection pillars, the hanging straps are respectively connected with hanging strap connection sleeves which are connected with the sealing box by interference fitting; the conductor wire is in communication with the controller, the sealing box is further internally provided with a positioning and sealing block for positioning and sealing the components therein; the controller, is internally provided with a time relay device, the controller controls the path of the alarm device to be turned on and off by the signal of the time relay.

Further, the inside of the locking outer plate is a locking cavity, the outer side of the locking outer plate is provided with an outer plate openable cover, and the inside of the locking outer plate is provided with a locking socket, the locking socket is plug-in fitted with a locking cylinder disposed on the middle of the outer side of the locking inner plate, in the middle of the outer part of the locking cylinder plate is provided with an annular slot, the locking cavity is provided with a clamping device fitting the annular slot in the outer side of the locking cylinder.

Further, the clamping device includes locking seats disposed within the locking cavity and located at both sides of the locking cylinder; each locking seat is interference fitted with a locking push column, and each locking push column is connected to a half locking sleeve fitting the locking cylinder, inner side of each half locking sleeve is connected to a half ring locking block, and the half ring locking block is plug-in fitted with the annular slot of the outer side of the locking cylinder.

Further, the inside of each half ring locking block is provided with a locking insert rod coaxial with the locking push column, the locking cylinder is provided with locking sockets connected to the annular slot and correspond to the locking insert rods.

Further, the length of the outer plate openable cover exceeds that of the locking cavity, and the outer plate openable cover is locked to the locking seat with openable cover locking bolts, the outer plate openable cover is provided with openable cover locking slots corresponding to the openable cover locking bolts, each locking push column is provided with holes plug-in fitted with the openable cover locking bolt, and the holes respectively correspond to the position where the half ring locking block is plugged into the annular slot and leaves the annular slot.

Further, the part where the two half ring locking blocks meet is interference fitted by the half ring sleeve insert rods.

THE BENEFICIAL EFFECTS OF THE INVENTION ARE

The control part of the power distribution control box is connected with the alarm device, and the display part of the power distribution control box displays the initial position. Therefore, it is convenient for people to find the patients and send them back, and the display part is sealed by a mechanical sealing structure and a glass plate, and the original position is displayed by a written paper, thereby saves energy consumption.

The structure of the locking barrier net can prevent the patients from unintentionally breaking up the glass, and thus avoid water leakage and destroy the cardboard.

The structure of the pressing holes and the display pressing springs can tightly seal the display sealing block and the display glass sleeves 37 together to avoid water leakage, and the design of the display pressing columns keeps the rear plate in position and seals the pressing holes.

The structure of the power distribution control box is ingeniously designed to achieve full sealing effect, and all components are sealed by a positioning and sealing block.

The locking cylinder and the annular slot provided on the outer side thereof together with the clamping may keep the locking inner plate and locking outer plate connected all the time, which can play a reinforcement effect on the interference fitting, avoiding the old people with dementia grabbing the device.

The structure of the clamping device is simple and convenient to operate, and can have a good clamping effect on the locking cylinder and the annular slot.

The structure of the locking insert rods can prevent the rotation of the locking cylinder and further improve the locking performance of the locking inner plate and locking outer plate.

The locking of the outer plate openable cover can position and lock the locking push columns, and it can also detect the locking position of the locking push columns, thereby the locking effect is ensured once again.

The structure of the half ring sleeve insert rods can reinforce the locking effect of the half ring locking blocks, meanwhile, by interference fitting with the locking half ring sleeves, the locking push columns can be held in position when inserting the openable locking bolts.

REFERENCE NUMBER KEY

The drawings includes following integers:
1—Power distribution control box;
2—Hanging strap;
3—Locking inner plate;
4—Locking outer plate;
5—Interference fitting pillar;
6—Alarm device;
7—Conductor wire;
8—Sealing box;
9—Box locking bolt;
10—Storage battery;
11—Positioning and sealing block;
12—Controller;
13—Battery connection pillar;
14—Hanging strap connection sleeve;
16—Outer plate openable cover;
17—Alarm connection column;
18—Locking cavity;
19—Locking cylinder;
20—Half locking sleeve;
21—Half ring locking block;
22—Locking insert rod;
23—Locking push column;
24—Locking seat;
25—Openable cover locking bolt;
26—Openable cover locking slot;
27—Half ring sleeve insert rod;
31—Display positioning sleeve;
32—Display press block;
33—Display pressing spring;
34—Display pressing column;
35—Display sealing block;
36—Sealing block locating pillar;
37—Display glass sleeve;
38—Display glass block;
39—Sealing block positioning convex ring;
40—Display barrier net;
41—Barrier locking bolt;
42—Display port.

DETAILED DESCRIPTION OF THE ILLUSTRATED EMBODIMENT

The present invention will be described in detail below with reference to the accompanying drawings, and the description of the present invention is only exemplary and explanatory, should not be construed as limiting the scope of the present invention.

Figure 1:
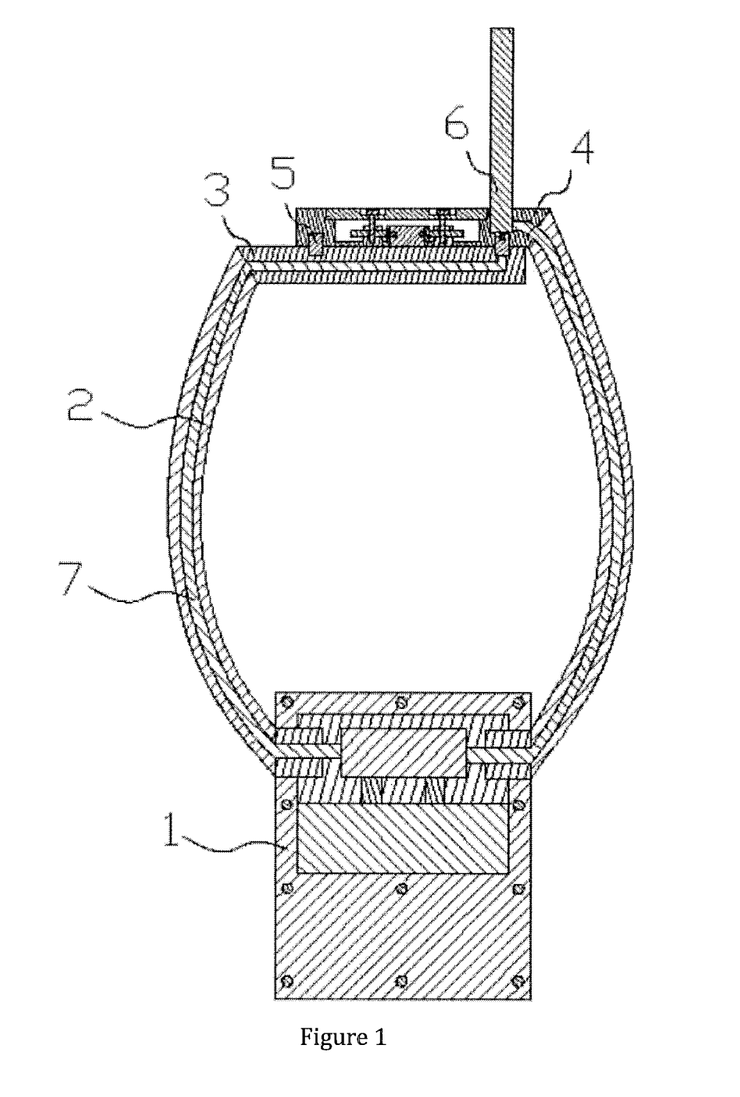
FIG. 1 is a patient with Alzheimer's disease positioning and retrieval assembly carrying an original location.
Figure 2:
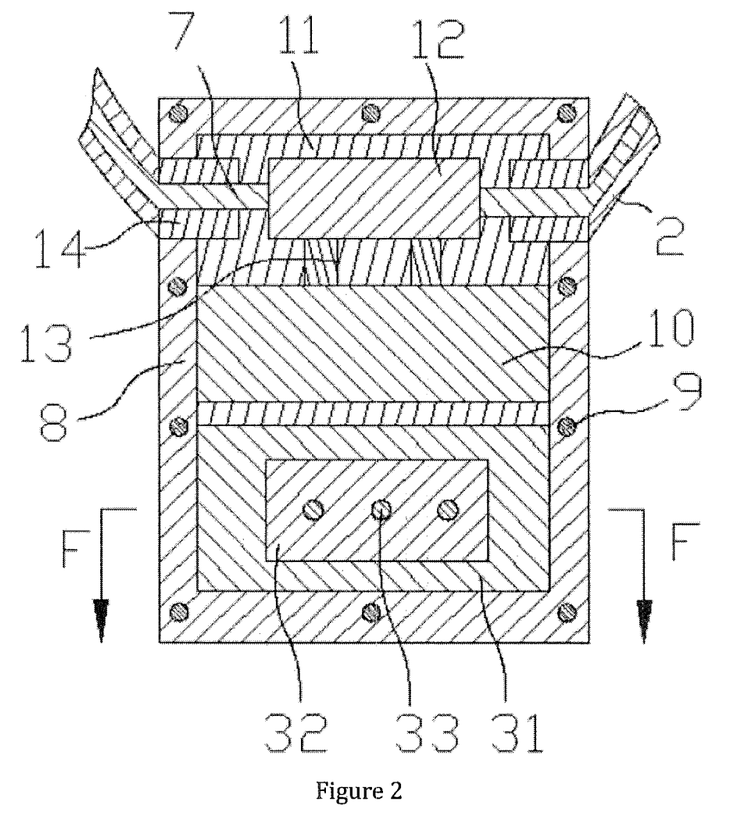
FIG. 2 is a schematic structural view of a power distribution control box.
Figure 3:
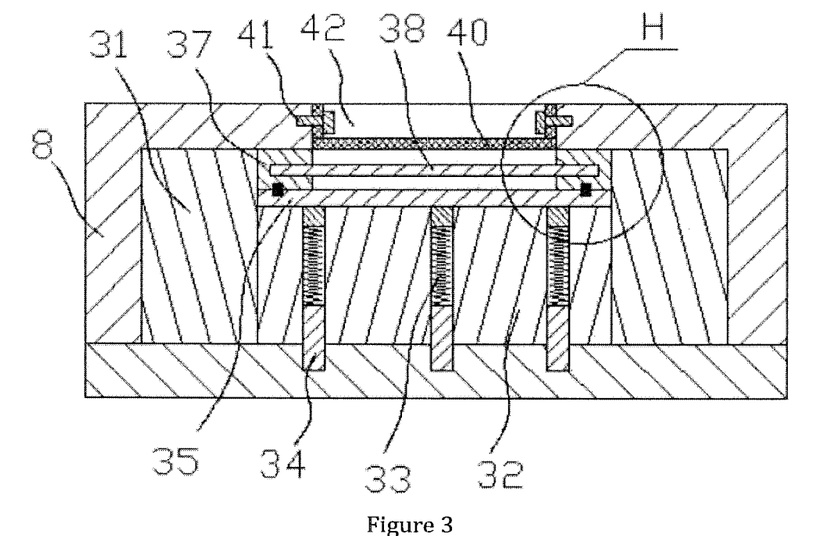
FIG. 3 is a cross-sectional view taken along line F-F of FIG. 2.

As shown in FIGS. 1-9, the specific structure of the present invention is as follows:

A patient with Alzheimer's disease positioning and retrieval assembly carrying an original location, including a power distribution control box 1 with hanging straps 2 attached to both sides thereof, the two hanging straps 2 are respectively connected with a locking outer plate 4 and a locking inner plate 3; the power distribution control box 1 includes a openable sealing box 8 locked by box locking bolts 9, the inner upper part of the sealing box 8 is a control part, the lower part of the sealing box 8 is a display part; the locking outer plate 4 is connected to an alarm device 6 communicating with the control part; the display part includes a display positioning sleeve 31 provided within the sealing box 8; the display positioning sleeve 31 is internally provided with a display glass sleeve 37, a display sealing block 35 and a display pressing column 34 from front to back; the front part of the display sealing blocks 35 is provided with sealing block positioning convex rings 39 plug-in fitted with the display glass sleeves 37; the display glass sleeve 37 is internally sleeved sealingly with a horizontal display glass block 38, a cardboard is disposed between the display sealing block 35 and the display glass block 38, the front panel of the sealing box 8 is provided with a display port 42 fitting the display glass block 38.

Preferably, a display barrier net 40 is fixedly connected to the display port 42 by barrier locking bolts 41, the mesh of the display barrier net 40 is smaller than dimension of fingertips.

Figure 4:
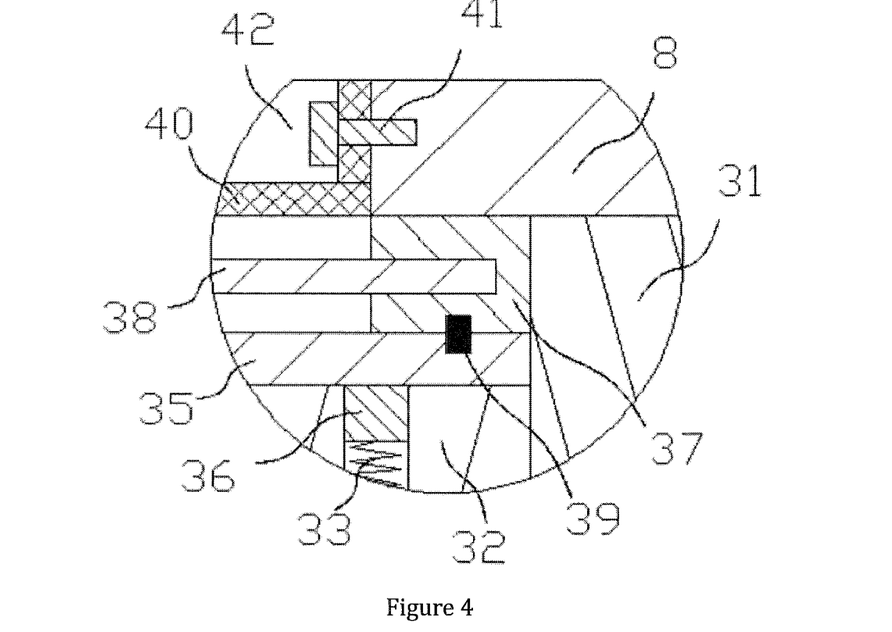
FIG. 4 is a partial enlarged view of region H in FIG. 3.

Preferably, the display press block 32 is internally provided with horizontally oriented pressing holes; the rear part of the display sealing block 35 is provided with sealing block locating pillars 36 plug-in fitted with the pressing holes, the rear side of the sealing block locating pillars 36 is provided with display pressing springs 33 in compression state, the rear side of the display pressing springs 33 is connected to display pressing pillars 34, which are sealingly fitted with the pressing holes and the rear ends thereof are inserted into the rear plate of the sealing box 8.

Figure 5:
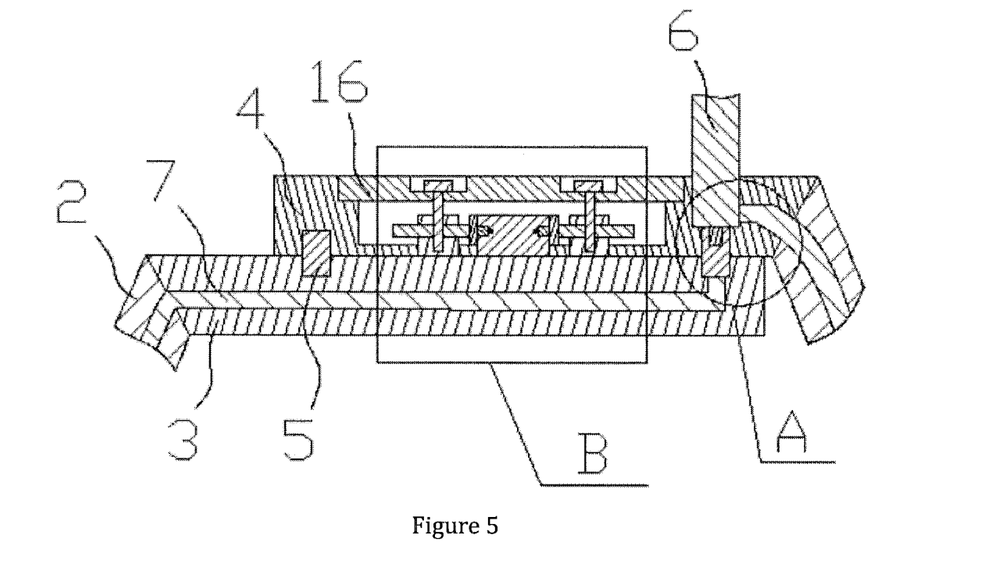
FIG. 5 is a schematic view showing the structure of the locking inner plate and locking outer plate.

Preferably, the outer ends of the locking inner plate 3 are provided with interference fitting pillars 5 interference fitting with the locking outer plate 4; one connection column of the alarm device 6 is connected to the control part by the locking outer plate 4 and a conductor wire 7 provided within the hanging strap 2, and another connection column thereof is interference fitted with the interference fitting pillar 5, and the interference fitting pillar 5 is connected to the control part by the locking inner plate 3 and the conductor wire 7 provided within the hanging strap 2, the control part is a power distribution control element that controls the alarm device 6 to operate intermittently.

Preferably, the control part includes a storage battery 10 disposed within the sealing box 8, the upper part of the storage battery 10 is connected to a controller 12 with battery connection pillars 13, the hanging straps 2 are respectively connected with hanging strap connection sleeves 14 which are connected with the sealing box 8 by interference fitting; the conductor wire 7 is in communication with the controller 12, the sealing box 8 is further internally provided with a positioning and sealing block 11 for positioning and sealing the components therein; the controller 12, is internally provided with a time relay device, the controller 12 controls the path of the alarm device 6 to be turned on and off by the signal of the time relay.

Figure 6:
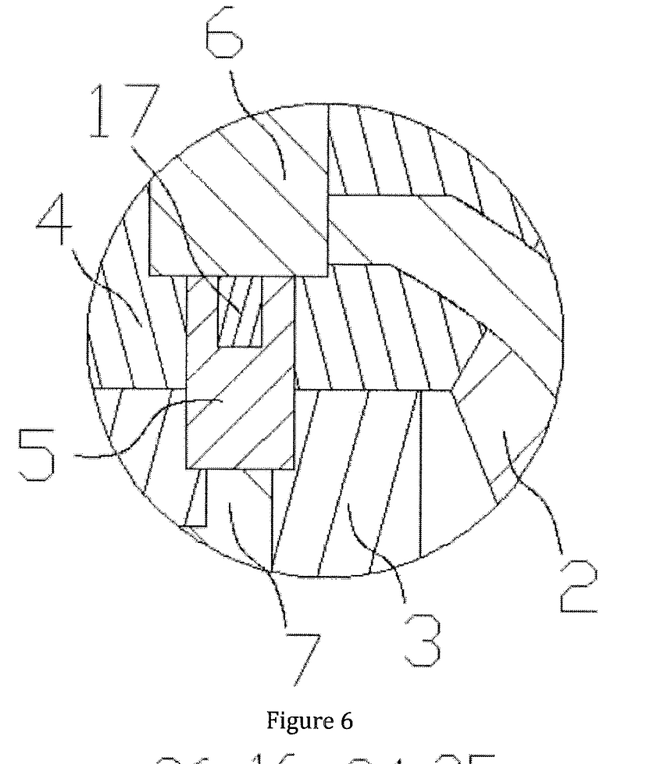
FIG. 6 is a partial enlarged view of part A in FIG. 5.

Preferably, the inside of the locking outer plate 4 is a locking cavity 18, the outer side of the locking outer plate 4 is provided with an outer plate openable cover 16, and the inside of the locking outer plate 4 is provided with a locking socket, the locking socket is plug-in fitted with a locking cylinder 19 disposed on the middle of the outer side of the locking inner plate 3, in the middle of the outer part of the locking cylinder 19 is provided with an annular slot, the locking cavity 18 is provided with a clamping device fitting the annular slot in the outer side of the locking cylinder 19.

Figure 7:
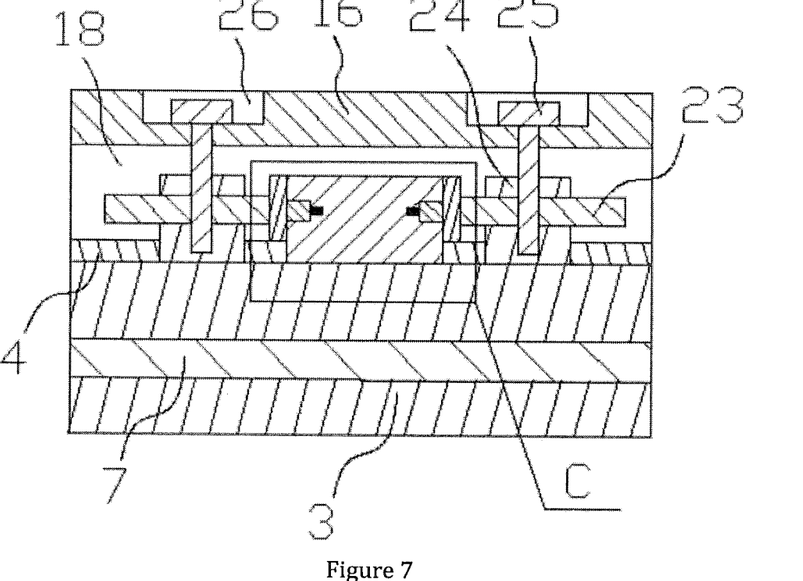
FIG. 7 is a partial enlarged view of part B in FIG. 5.
Figure 8:
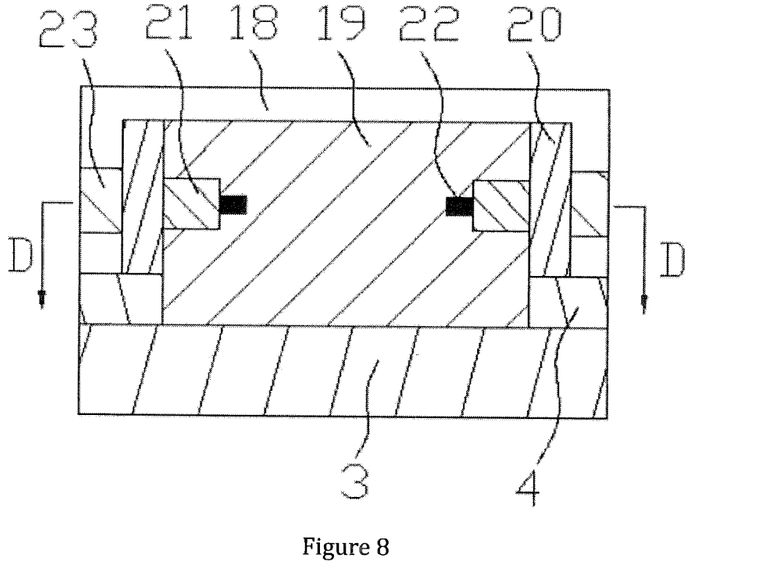
FIG. 8 is a partial enlarged view of part C in FIG. 7.

Preferably, the clamping device includes locking seats 24 disposed within the locking cavity 18 and located at both sides of the locking cylinder 19; each locking seat 24 is interference fitted with a locking push column 23, and each locking push column 23 is connected to a half locking sleeve 20 fitting the locking cylinder 19, inner side of each half locking, sleeve 20 is connected to a half ring locking block 21, and the half ring locking block 21 is plug-in fitted with the annular slot of the outer side of the locking cylinder 19.

Figure 9:
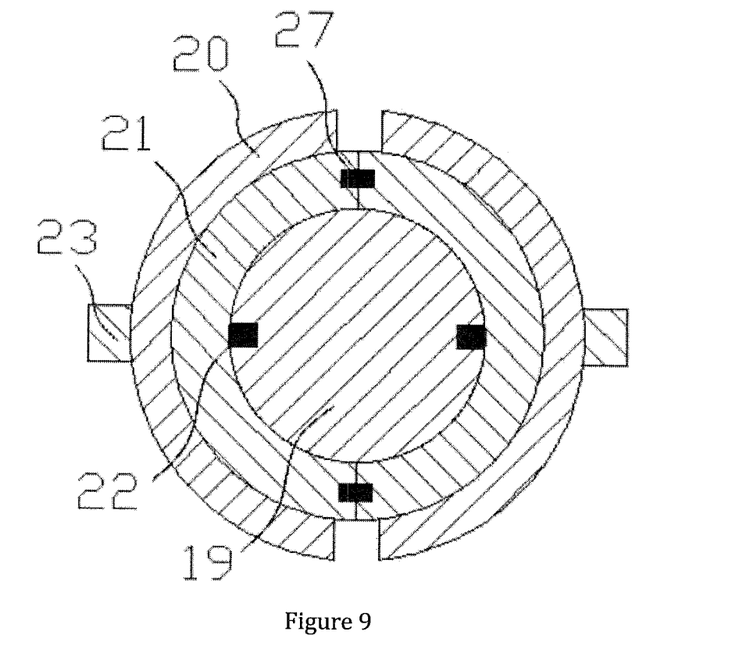
FIG. 9 is a cross-sectional view taken along line D-D of FIG. 8.

Preferably, the inside of each half ring locking block 21 is provided with a locking insert rod 22 coaxial with the locking push column 23, the locking cylinder 19 is provided with locking sockets connected to the annular slot and correspond to the locking insert rods 22.

Preferably, the length of the outer plate openable cover 16 exceeds that of the locking cavity 18, and the outer plate openable cover 16 is locked to the locking seat 24 with openable cover locking bolts 25, the outer plate openable cover 16 is provided with openable cover locking slots 26 corresponding to the openable cover locking bolts 25, each locking push column 23 is provided with 2 holes plug-in fitted with the openable cover locking bolt 25, and the 2 holes respectively correspond to the position where the half ring locking block 21 is plugged into the annular slot and leaves the annular slot.

Preferably, the part where the two half ring locking blocks 21 meet is interference fitted by the half ring sleeve insert rods 27. When in specific use, first adjust the interval of the signal time of the time relay, usually the signal is sent once every 2 hours. Open the sealing box 8, place the display glass covers 37 with the display glass plate 38 mounted in the display positioning sleeve 31; put the cardboard with the initial address and family member phone number into the display glass block 38, place the display sealing block 35 in position, then the display press block 32; insert the sealing block locating pillars 36 into the pressing holes, close the rear cover of the sealing box 8 onto the display pressing columns 34 to complete positioning, and seal the sealing box 8 with the box locking bolts, and then put the mechanism around the neck of the patient; during wearing, insert the interference fitting pillars 5 first into the locking outer plate 4, and insert the battery connection pillar 13 into one of the interference fitting pillars 5 to achieve the communication; then disconnect the openable cover locking bolts 25 on the outer plate openable cover 16, and remove the outer plate openable cover 16; by pushing the locking push column 23 inwardly the half locking sleeve 20 is sleeved on the outside of the locking cylinder 19 and the half ring locking blocks 21 are inserted into the annular slot, and the locking insert rods 22 are inserted into the locking sockets; the two half ring locking blocks 21 are interference sleeved with each other by the half ring sleeve insert rods 27, thereby completes the locking of the locking push column 23; close the outer plate openable cover 16, and lock it with the openable cover locking bolts 25 and the locking seats 24; during locking, the openable cover locking bolts 25 pass through the locking push column 23 to lock the locking pushing columns 23, if any of the locking push columns 23 cannot be locked, it is not in place and needs adjustment and locking again, when finishing wearing, the device can be used. If the wearer is lost, the controller 12 controls the alarm 6 to issue an alarm of about two minutes every 2 hours according to the signal of the time relay, which enables the surrounding people to find the lost wearer in time and call the police or contact the phone number in the cardboard to send him/her back. In most cases, the wearer can be found and reported to the police after three alarms, that is, within six hours. As a result, the wearer is not far away, which greatly improves the efficiency of finding him/her.

It is to be the that the terms "includes" "including" or any other variants thereof are intended to encompass a non-exclusive inclusion, such that a process, method, article, or device comprising a plurality of elements includes not only those elements, but also other elements that are not explicitly listed, or elements that are inherent to such a process, method, item, or device.

The principles and embodiments of the present invention have been described herein with reference to specific examples. The description of the above examples is only to aid in understanding the method of the present invention and core idea thereof. The above description is only a preferred embodiment of the present invention, and it should be noted that due to the finiteness of the textual expression, there is an infinitely specific structure objectively, those skill in the art can also make a number of improvements, modifications, or variations without departing from the principles of the invention, and the above technical features may be combined in an appropriate manner; these improvements, modifications, variation or combination, or unmodified, directly apply the inventive concept and technical solution to other occasions all should be considered as the scope of protection of the present invention.

What is claimed is:

1. A patient with Alzheimer's disease positioning and retrieval assembly carrying an original location, including a power distribution control box (1) with hanging straps (2) attached to both sides thereof, the two hanging straps (2) are respectively connected with a locking outer plate (4) and a locking inner plate (3); the power distribution control box (1) includes a openable sealing box (8) locked by box locking bolts (9), the inner upper part of the sealing box (8) is a control part, the lower part of the sealing box (8) is a display part; the locking outer plate (4) is connected to an alarm device (6) communicating with the control part; the display part includes a display positioning sleeve (31) provided within the sealing box (8); the display positioning sleeve (31) is internally provided with a display glass sleeve (37), a display sealing block (35) and a display pressing column (34) from front to back; the front part of the display sealing blocks (35) is provided with sealing block positioning convex rings (39) plug-in fitted with the display glass sleeves (37); the display glass sleeve (37) is internally sleeved sealingly with a horizontal display glass block (38), a cardboard is disposed between the display sealing block (35) and the display glass block (38), the front panel of the sealing box (8) is provided with a display port (42) fitting the display glass block (38).

2. The patient with Alzheimer's disease positioning and retrieval assembly carrying an original location of claim 1, wherein a display barrier net (40) is fixedly connected to the display port (42) by barrier locking bolts (41), the mesh of the display barrier net (40) is smaller than dimension of fingertips.

3. The patient with Alzheimer's disease positioning and retrieval assembly carrying an original location of claim 1, wherein the display press block (32) is internally provided with horizontally oriented pressing holes; the rear part of the display sealing block (35) is provided with sealing block locating pillars (36) plug-in fitted with the pressing holes, the rear side of the sealing block locating pillars (36) is provided with display pressing springs (33) in compression state, the rear side of the display pressing springs (33) is connected to display pressing pillars (34), which are sealingly fitted with the pressing holes and the rear ends thereof are inserted into the rear plate of the sealing box (8).

4. The patient with Alzheimer's disease positioning and retrieval assembly carrying an original location of claim 1, wherein the outer ends of the locking inner plate (3) are provided with interference fitting pillars (5) interference fitting with the locking outer plate (4); one connection column of the alarm device (6) is connected to the control part by the locking outer plate (4) and a conductor wire (7) provided within the hanging strap (2), and another connection column thereof is interference fitted with the interference fitting pillar (5), and the interference fitting pillar (5) is connected to the control part by the locking inner plate (3) and the conductor wire (7) provided within the hanging strap (2), the control part is a power distribution control element that controls the alarm device (6) to operate intermittently.

5. The patient with Alzheimer's disease positioning and retrieval assembly carrying an original location of claim 4, wherein the control part includes a storage battery (10) disposed within the sealing box (8), the upper part of the storage battery (10) is connected to a controller (12) with battery connection pillars (13), the hanging straps (2) are respectively connected with hanging strap connection sleeves (14) which are connected with the sealing box (8) by interference fitting; the conductor wire (7) is in communication with the controller (12), the sealing box (8) is further internally provided with a positioning and sealing block (11) for positioning and sealing the components therein; the controller (12), is internally provided with a time relay device, the controller (12) controls the path of the alarm device (6) to be turned on and off by the signal of the time relay.

6. The patient with Alzheimer's disease positioning and retrieval assembly carrying an original location of claim 4, wherein the inside of the locking outer plate (4) is a locking cavity (18), the outer side of the locking outer plate (4) is provided with an outer plate openable cover (16), and the inside of the locking outer plate (4) is provided with a locking socket, the locking socket is plug-in fitted with a locking cylinder (19) disposed on the middle of the outer side of the locking inner plate (3), in the middle of the outer part of the locking cylinder (19) is provided with an annular slot, the locking cavity (18) is provided with a clamping device fitting the annular slot in the outer side of the locking cylinder (19).

7. The patient with Alzheimer's disease positioning and retrieval assembly carrying an original location of claim 6, wherein the clamping device includes locking seats (24) disposed within the locking cavity (18) and located at both sides of the locking cylinder (19); each locking seat (24) is interference fitted with a locking push column (23), and each locking push column (23) is connected to a half locking sleeve (20) fitting the locking cylinder (19), inner side of each half locking sleeve (20) is connected to a half ring locking block (21), and the half ring locking block (21) is plug-in fitted with the annular slot of the outer side of the locking cylinder (19).

8. The patient with Alzheimer's disease positioning and retrieval assembly carrying an original location of claim 7, wherein the inside of each half ring locking block (21) is provided with a locking insert rod (22) coaxial with the locking push column (23), the locking cylinder (19) is provided with locking sockets connected to the annular slot and correspond to the locking insert rods (22).

9. The patient with Alzheimer's disease positioning and retrieval assembly carrying an original location of claim 8, wherein the length of the outer plate openable cover (16) exceeds that of the locking cavity (18), and the outer plate openable cover (16) is locked to the locking seat (24) with openable cover locking bolts (25), the outer plate openable cover (16) is provided with openable cover locking slots (26) corresponding to the openable cover locking bolts (25), each locking push column(23) is provided with 2 holes plug-in fitted with the openable cover locking bolt (25), and the 2 holes respectively correspond to the position where the half ring locking block (21) is plugged into the annular slot and leaves the annular slot.

10. The patient with Alzheimer's disease positioning and retrieval assembly carrying an original location of claim 9, wherein the part where the two half ring locking blocks (21) meet is interference fitted by the half ring sleeve insert rods (27).

* * * * *